Oct. 20, 1959 R. V. LINDQUIST Plant Pat. 1,873
ROSE PLANT
Filed Feb. 2, 1959
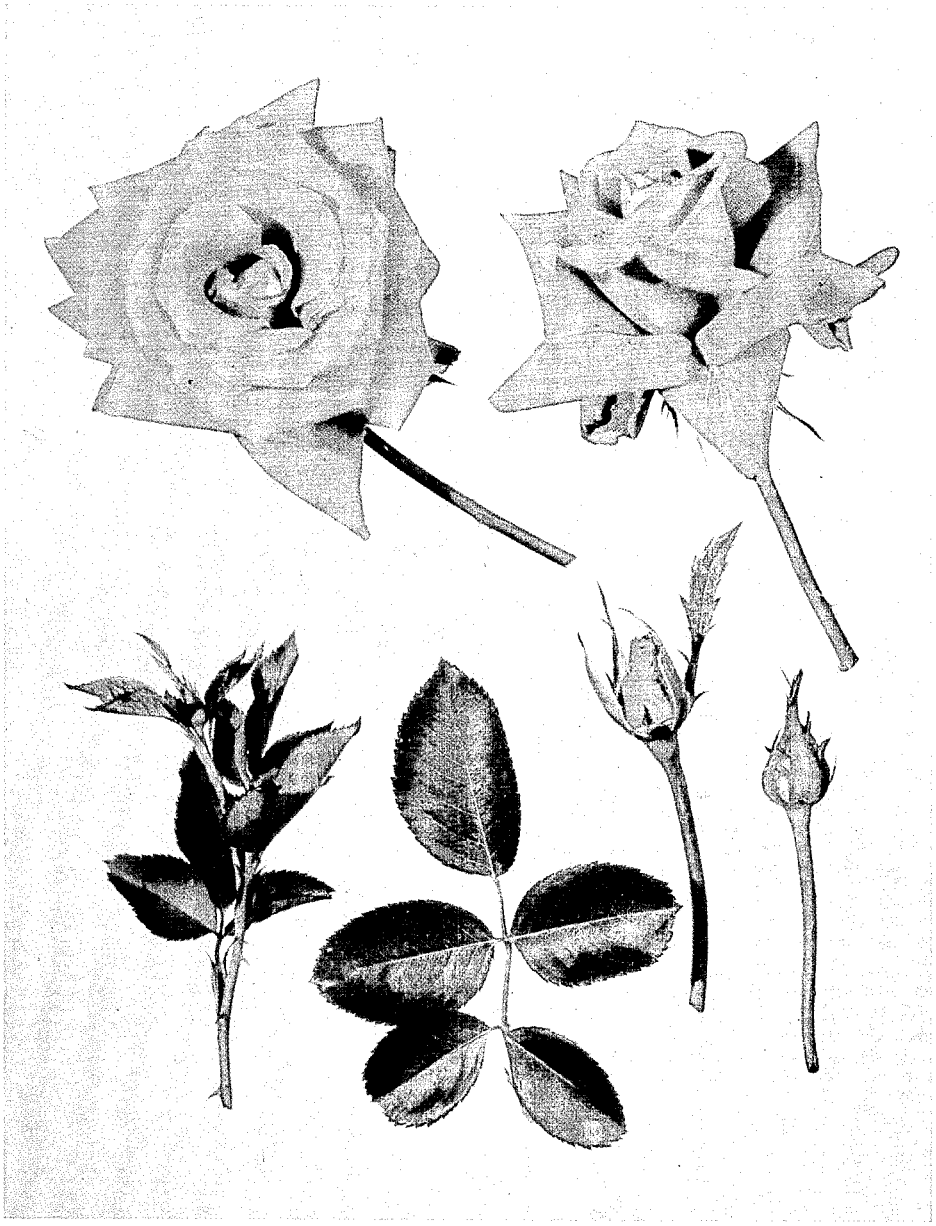
INVENTOR
R. V. Lindquist
BY Robb & Robb
ATTORNEYS United States Patent Office Plant Pat. 1,873

Patented Oct. 20, 1959

1,873

ROSE PLANT

Robert V. Lindquist, Hemet, Calif., assignor to Hemet Wholesale, Hemet, Calif., a partnership Application February 2, 1959, Serial No. 790,401

1 Claim. (Cl. 47—61)

The present invention relates to a new and distinct variety of rose plant of the hybrid polyantha (grandiflora) class, which was originated by me by crossing the variety "Tiffany" (Plant Patent No. 1,304) with the variety "Baby Chateau" (unpatented).

As the result of this breeding, I have produced a new rose variety which is particularly characterized as to novelty by the following unique combination of characteristics which are outstanding in the new variety and which distinguish it from its parents, as well as from all other varieties of which I am aware:

(1) Freedom of bloom;

(2) Exceptionally well-formed flowers;

(3) An unusual and distinctive raspberry fragrance of the flowers; and (4) A distinctive Rose Red general color tonality of the flowers.

Asexual reproduction of my new variety by budding, as performed at Hemet, California, shows that the foregoing characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with Robert F. Wilson's Horticultural Colour Chart (hereinafter abbreviated as "Wilson") and Ridgway's Color Standards and Nomenclature (hereinafter abbreviated as "Ridgway"):

Type: Half-hardy; tall; bush; for cut flowers and for garden decoration.

Class:

*Botanical.*—Hybrid polyantha.

*Commercial.*—Grandiflora.

Breeding: Seedling.

*Seed parent.*—"Tiffany."

*Pollen parent.*—"Baby Chateau."

Propagation: Holds its distinguishing characteristics through succeeding propagations by budding.

*Flower*

Locality where grown and observed: Hemet, California.

Flowers borne: Usually singly; on stems of normal strength and from medium length to long.

Quantity of bloom: Free, outdoors.

Continuity: Continuous during growing season.

Fragrance: Slight. Nature—raspberry.

Bud:

*Peduncle.*—Average length; average caliper; erect; moderately smooth; few gland-tipped cilia, and few hairs and prickles. Color—near Biscay Green, Plate XVII (Ridgway).

*Before calyx breaks.*—Size—medium. Form—medium length; ovoid; with foliaceous appendages, and few gland-tipped cilia on the surface of the bud; usually with slender foliaceous parts extending beyond the tip of the bud equal to ½ or more of its length.

*As calyx breaks.*—Color—near Rose Red, Plate 724, page 158 (Wilson).

*Sepals.*—Inner surface—with fine, woolly tomentum. Margins—with foliaceous appendages and gland-tipped cilia.

*As first petal opens.*—Size—average. Form—medium length; pointed. Color: outside—near Rose Red, Plate 724/1, page 158 (Wilson), with base near Canary Yellow, Plate 2/3, page 2 (Wilson); inside—near Rose Red, Plate 724, page 158 (Wilson), with base near Canary Yellow, Plate 2/3, page 2 (Wilson).

*Opening.*—Opens up well; is not retarded from opening by cold, hot, wet or dry weather.

Bloom:

*Size (when fully open).*—From 3 inches to 4 inches.

*Petalage.*—Double; from 25 to 30 petals, plus from 3 to 5 petaloids; arranged regularly.

*Form.*—High-centered at first, but becoming somewhat cupped; petals being at first rolled outward, but becoming later at maturity less cupped, with tips rolled outward.

Petals:

*Texture.*—medium. Inside—velvety. Outside—satiny.

*Shape.*—Outer—round. Intermediate.—oval, with apex rounded. Inner—nearly oval.

This description of a newly opened flower was made from a rose grown outdoors in the month of October at Hemet, California:

*Color.*—Outer petal: outside surface—near Rose Red, Plate 724/1, page 158 (Wilson), with base near Canary Yellow, Plate 2/3, page 2 (Wilson); inside surface—near Rose Red, Plate 724, page 158 (Wilson), with base near Canary Yellow, Plate 2/3, page 2 (Wilson). Intermediate petal: outside surface—near Rose Red, Plate 725/1, page 158 (Wilson), with base near Canary Yellow, Plate 2/3, page 2 (Wilson); inside surface—near Rose Red, Plate 724, page 158 (Wilson), with base near Canary Yellow, Plate 2/3, page 2 (Wilson). Inner petal: outside surface—near Rose Red, Plate 724/2, page 158 (Wilson), with base near Canary Yellow, Plate 2/3, page 2 (Wilson); inside surface—near Rose Red, Plate 724/1, page 158 (Wilson), with base near Canary Yellow, Plate 2/3, page 2 (Wilson).

This description was made from a rose that was open for 3 days outdoors in the month of October at Hemet, California:

*Color.*—Outer petal: outside surface—near Rose Red, Plate 724/2, page 158 (Wilson), with base near Canary Yellow, Plate 2/3, page 2 (Wilson); inside surface—near Rose Red, Plate 724, page 158 (Wilson), with base near Canary Yellow, Plate 2/3, page 2 (Wilson). Inner petal: outside surface—near Rose Red, Plate 724/2, page 158 (Wilson), with base near Canary Yellow, Plate 2/3, page 2 (Wilson); inside surface—near Rose Red, Plate 724/1, page 158 (Wilson), with base near Canary Yellow, Plate 2/3, page 2 (Wilson).

*General color effect.*—Newly opened flower—from near Rose Red, Plate 724, page 158 (Wilson) to near Rose Red, Plate 724/1, page 158 (Wilson). 3-days open—from near Rose Red, Plate 724, page 158 (Wilson) to near Rose Red, Plate 724/2, page 158 (Wilson).

*Behavior.*—Drop off cleanly.

*Flower longevity.*—On bush in garden—3 or 4 days in October. Cut roses grown outdoors and kept at living-room temperatures—3 or 4 days in October.

*Reproductive organs*

Stamens: Average number; arranged regularly about pistils; a few mixed with petaloids.

Filaments: Medium length; most with anthers. Color—at base near Rose Opal, Plate 022/1, page 110 (Wilson), shading to near Aureolin, Plate 3/2, page 3 (Wilson).

Anthers: Medium size; all open approximately at once. Color: upper side—near Orange Buff, Plate 507, page 133 (Wilson); under side —near Orange Buff, Plate 507, page 133 (Wilson).

Pollen: Moderate. Color—near Indian Yellow, Plate 6/1, page 6 (Wilson).

Pistils: Many; approximately 90 to 125 in number.

Styles: Moderately uneven; from short to average length; bunched.

Stigma: Color—near Orange Buff, Plate 507/2, page 133 (Wilson).

Ovaries: Usually most protruding from calyx.

Hips: None.

Sepals: Falling soon; medium length; spear-shaped. Color: inside—near Light Turtle Green, Plate XXXII (Ridgway); outside—near Light Bice Green, Plate XVII (Ridgway).

Seeds: None.

*Plant*

Foliage:

*Leaves.*—Compound of usually 3 to 7 leaflets; normal abundance; from medium size to large; somewhat leathery; semi-glossy.

*Leaflets.*—Shape—oval, with apex of some leaves obtuse and some acute. Base—round. Margin—serrate.

*Color.*—Mature: upper surface—near Empire Green, Plate XXXII (Ridgway); under surface—near Bice Green, Plate XVII (Ridgway). Young: upper surface—near Elm Green, Plate XVII (Ridgway); shading to near Dark Corinthian Purple, Plate XXXVIII (Ridgway); under surface—near Dark Corinthian Purple, Plate XXXVIII (Ridgway).

*Rachis (the supporting stem of the compound leaf).*—Average size. Upper side—grooved, with few stipitate glands on edges. Under side—moderately prickly, with few stipitate glands.

*Stipules.*—Medium length; medium width; with medium length points turning out at an angle of about 45°.

*Disease resistance.*—Mildly subject to mildew, as determined by comparison with other varieties grown under comparable cultural conditions at Hemet, California.

Growth:

*Habit.*—Upright; much-branched.

*Growth.*—Very vigorous.

*Canes.*—Medium caliper.

*Main stems.*—Color—near Bice Green, Plate XVII (Ridgway). Large prickles—several; from medium length to long; hooked slightly downward; with medium length, moderately broad base; color—near Cinnamon Brown, Plate XV (Ridgway). Small prickles—several; color—near Cinnamon Brown, Plate XV (Ridgway). Hairs—few; color—near Cinnamon Brown, Plate XV (Ridgway).

*Branches.*—Color—near Light Bice Green, Plate XVII (Ridgway). Large prickles—several; from medium length to long; hooked slightly downward; with medium length, moderately broad base; color—near Cinnamon Brown, Plate XV (Ridgway). Small prickles—several; color—near Cinnamon Brown, Plate XV (Ridgway). Hairs—few; color—near Cinnamon Brown, Plate XV (Ridgway).

*New shoots.*—Color—near Biscay Green, Plate XVII (Ridgway), with occasional shadings of near Corinthian Purple, Plate XXXVIII (Ridgway). Large prickles—several; medium length; hooked slightly downward; with medium length, moderately broad base; color—near Liver Brown, Plate XIV (Ridgway). Small prickles—several; color—near Liver Brown, Plate XIV (Ridgway). Hairs—few; color—near Liver Brown, Plate XIV (Ridgway).

I claim:

A new and distinct variety of rose plant of the hybrid polyantha (grandiflora) class, substantially as herein shown and described, characterized particularly as to novelty by the unique combination of freedom of bloom, exceptionally well-formed flowers, an unusual and distinctive raspberry fragrance of the flowers, and a distinctive Rose Red general color tonality of the flowers.

No references cited.